(12) United States Patent  
Chuter et al.

(10) Patent No.: US 9,119,742 B2  
(45) Date of Patent: Sep. 1, 2015

(54) PROSTHESIS DELIVERY AND DEPLOYMENT DEVICE

(75) Inventors: Timothy A. Chuter, San Francisco, CA (US); David D. Grewe, West Lafayette, IN (US); Blayne A. Roeder, Lafayette, IN (US); Alan R. Leewood, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 931 days.

(21) Appl. No.: 12/173,277

(22) Filed: Jul. 15, 2008

(65) Prior Publication Data

US 2009/0024137 A1 Jan. 22, 2009

Related U.S. Application Data

(60) Provisional application No. 60/950,001, filed on Jul. 16, 2007.

(51) Int. Cl.
*A61F 2/966* (2013.01)
*A61F 2/95* (2013.01)

(52) U.S. Cl.
CPC . *A61F 2/966* (2013.01); *A61F 2/95* (2013.01); *A61F 2002/9517* (2013.01)

(58) Field of Classification Search
CPC .... A61F 2/95; A61F 2002/9517; A61F 2/966
USPC ........ 606/108, 191, 194, 200; 623/1.11, 1.12, 623/1.23, 2.11, 6.12
See application file for complete search history.

(56) References Cited

U.S. PATENT DOCUMENTS

| | | |
|---|---|---|
| 4,562,596 A | 1/1986 | Kornberg |
| 4,665,918 A | 5/1987 | Garza et al. |
| 4,921,484 A | 5/1990 | Hillstead |
| 5,078,720 A | 1/1992 | Burton et al. |
| 5,092,877 A | 3/1992 | Pinchuk |
| 5,201,757 A | 4/1993 | Heyn et al. |
| 5,380,304 A | 1/1995 | Parker |
| 5,415,664 A | 5/1995 | Pinchuk |
| 5,445,646 A | 8/1995 | Euteneuer et al. |
| 5,534,007 A | 7/1996 | St. Germain et al. |
| 5,626,603 A | 5/1997 | Venturelli et al. |

(Continued)

FOREIGN PATENT DOCUMENTS

| | | |
|---|---|---|
| EP | 0 696 447 B1 | 2/1996 |
| EP | 1 078 611 A1 | 2/2001 |

(Continued)

OTHER PUBLICATIONS

International Search Report for International Application No. PCT/US2008/008677.

(Continued)

*Primary Examiner* — Sarah W Aleman  
(74) *Attorney, Agent, or Firm* — Brinks Gilson & Lione

(57) ABSTRACT

A device for delivering and deploying a prosthesis is described and comprises an elongate sheath having a sheath lumen and a delivery catheter slidably disposed within the sheath lumen. A deployment assist mechanism may be coupled to the delivery catheter and the sheath and configured to apply a retraction force to the delivery catheter and the sheath. Additional devices, systems, and methods of delivering and deploying a prosthesis are described.

19 Claims, 9 Drawing Sheets

(56) References Cited

U.S. PATENT DOCUMENTS

| | | | |
|---|---|---|---|
| 5,683,451 A | 11/1997 | Lenker et al. | |
| 5,690,644 A | 11/1997 | Yurek et al. | |
| 5,693,086 A | 12/1997 | Goicoechea et al. | |
| 5,817,101 A | 10/1998 | Fiedler | |
| 5,824,041 A | 10/1998 | Lenker et al. | |
| 5,906,619 A | 5/1999 | Olson et al. | |
| 5,968,052 A | 10/1999 | Sullivan, III et al. | |
| 6,004,328 A | 12/1999 | Solar | |
| 6,024,763 A | 2/2000 | Lenker et al. | |
| 6,056,759 A | 5/2000 | Fiedler | |
| 6,113,608 A | 9/2000 | Monroe et al. | |
| 6,123,723 A | 9/2000 | Konya et al. | |
| 6,203,550 B1 | 3/2001 | Olson | |
| 6,206,888 B1* | 3/2001 | Bicek et al. | 606/108 |
| 6,254,611 B1 | 7/2001 | Vrba | |
| 6,287,315 B1 | 9/2001 | Wijeratne et al. | |
| 6,350,278 B1 | 2/2002 | Lenker et al. | |
| 6,402,760 B1* | 6/2002 | Fedida | 606/108 |
| 6,514,261 B1 | 2/2003 | Randall et al. | |
| 6,579,297 B2 | 6/2003 | Bicek et al. | |
| 6,599,296 B1* | 7/2003 | Gillick et al. | 606/108 |
| 6,605,109 B2 | 8/2003 | Fiedler | |
| 6,626,934 B2 | 9/2003 | Blaeser et al. | |
| 6,652,480 B1 | 11/2003 | Imran et al. | |
| 6,669,716 B1 | 12/2003 | Gilson et al. | |
| 6,849,084 B2 | 2/2005 | Rabkin et al. | |
| 6,858,034 B1 | 2/2005 | Hijlkema et al. | |
| 6,911,039 B2 | 6/2005 | Shiu et al. | |
| 7,105,016 B2 | 9/2006 | Shiu et al. | |
| 7,122,050 B2 | 10/2006 | Randall et al. | |
| 7,419,501 B2 | 9/2008 | Chiu et al. | |
| 2001/0012944 A1 | 8/2001 | Bicek et al. | |
| 2001/0034514 A1 | 10/2001 | Parker | |
| 2002/0045929 A1 | 4/2002 | Diaz | |
| 2003/0028236 A1* | 2/2003 | Gillick et al. | 623/1.11 |
| 2003/0109886 A1 | 6/2003 | Keegan et al. | |
| 2004/0093063 A1 | 5/2004 | Wright et al. | |
| 2004/0098079 A1 | 5/2004 | Hartley et al. | |
| 2004/0106974 A1 | 6/2004 | Greenberg et al. | |
| 2004/0127912 A1 | 7/2004 | Rabkin et al. | |
| 2004/0133264 A1 | 7/2004 | Moore | |
| 2004/0148008 A1 | 7/2004 | Goodson, IV et al. | |
| 2005/0060018 A1 | 3/2005 | Dittman | |
| 2005/0080476 A1 | 4/2005 | Gunderson et al. | |
| 2005/0085890 A1 | 4/2005 | Rasmussen et al. | |
| 2005/0090887 A1 | 4/2005 | Pryor | |
| 2005/0273151 A1 | 12/2005 | Fulkerson et al. | |
| 2006/0142833 A1* | 6/2006 | Von Oepen et al. | 623/1.11 |
| 2006/0282150 A1 | 12/2006 | Olson et al. | |
| 2006/0282152 A1 | 12/2006 | Beyerlein et al. | |
| 2006/0286145 A1 | 12/2006 | Horan et al. | |
| 2007/0060999 A1 | 3/2007 | Randall et al. | |
| 2007/0233222 A1 | 10/2007 | Roeder et al. | |
| 2007/0255390 A1 | 11/2007 | Ducke et al. | |
| 2007/0293934 A1 | 12/2007 | Grewe | |
| 2008/0021538 A1 | 1/2008 | Wright et al. | |

FOREIGN PATENT DOCUMENTS

| | | |
|---|---|---|
| WO | WO 95/11055 A1 | 4/1995 |
| WO | WO 98/53761 A1 | 12/1998 |
| WO | WO 2005/107644 A1 | 11/2005 |
| WO | WO 2007/084370 A1 | 7/2007 |

OTHER PUBLICATIONS

Written Opinion of the International Search Authority for International Application No. PCT/US2008/008677.

\* cited by examiner

PROSTHESIS DELIVERY AND DEPLOYMENT DEVICE

RELATED APPLICATIONS

This patent document claims the benefit of the filing date under 35 U.S.C. §119(e) of U.S. Provisional Patent Application Ser. No. 60/950,001, filed Jul. 16, 2007 which is herein incorporated by reference in its entirety.

BACKGROUND OF THE INVENTION

1. Field of the Invention

This invention relates to a medical device and, in particular, to a delivery and deployment device for a prosthesis and a method of deploying a prosthesis in a body lumen.

2. Description of Related Art

Endoluminal prostheses, such as stents and stent grafts, are used for treating damaged or diseased body lumens such as the esophagus, bile duct, and blood vessels. For example, endoluminal prostheses may be used for repairing diseased aortas including abdominal aortic aneurysms and thoracic aortic aneurysms. Such a prosthesis is placed inside the body lumen and provides some or all of the functionality of the original, healthy vessel.

The deployment of endoluminal prostheses into the lumen of a patient from a remote location by the use of a catheter delivery and deployment device is well known in the art. For example, PCT Patent Publication Number WO 98/53761 entitled "A Prosthesis and a Method and Means of Deploying a Prosthesis," which is incorporated herein by reference, proposes a deployment system for an endoluminal prosthesis. The prosthesis is radially compressed onto a delivery catheter and is covered by an outer sheath. To deploy the system, the operator slides or retracts the outer sheath over the delivery catheter, thereby exposing the prosthesis. The prosthesis expands outwardly upon removal of the sheath. Such a delivery and deployment device has been referred to as a "push-pull" system because as the operator pulls the sheath proximally in relation to the delivery catheter, the delivery catheter pushes the prosthesis out of the sheath.

Devices, such as the ones described in WO 98/53761 have several advantages. To deploy the prosthesis, the operator can directly manipulate the sheath and the delivery catheter. This provides the operator with a relatively high degree of control during the procedure. Further, such devices may be compact and may have a relatively uniform, low-diameter radial profile, allowing for atraumatic access and delivery.

In order to provide a low-diameter profile, the delivery catheter, the sheath, and the prosthesis are often very tightly interconnected. As a result, manual retraction of the sheath may be challenging. An exemplary delivery and deployment device may require as much as 100 Newtons (N) or approximately 22.5 pounds of force to deploy. Such resistance can easily tire an operator and accordingly is highly undesireable.

SUMMARY

Various devices that may be provided for delivering and deploying a prosthesis are disclosed throughout the specification and in the drawings. In one example, a device for delivering and deploying a prosthesis may be provided and comprise an elongate sheath having a sheath lumen, a delivery catheter slidably disposed within the sheath lumen, and a deployment assist mechanism coupled to the delivery catheter and the sheath and configured to apply a retraction force to the delivery catheter and the sheath. The sheath is retractable over the delivery catheter over a retraction distance and the device has a retraction resistance.

In some examples, the retraction force applied by the assist mechanism may be less than or equal to the retraction resistance over at least a portion of the retraction distance. Accordingly, the retraction force may be insufficient to retract the sheath and an additional force, such as a manual retraction force, may be required to retract the sheath. In some examples, the retraction force applied by the assist mechanism may be greater than or equal to the retraction resistance over at least another portion of the retraction distance. Accordingly, an additional force may be required to retract the sheath over one portion of the retraction distance, whereas no additional force may be required to retract the sheath over another portion of the retraction distance.

In some examples, the retraction resistance may decrease as the sheath is retracted over the delivery catheter. Additionally, or alternatively, the retraction force provided by the assist mechanism may decrease as the sheath is retracted over the delivery catheter.

The assist mechanism may comprise a stored energy device, such as a spring. A spring may comprise, for example, one or more coil springs and/or one or more gas springs. In some examples, the assist mechanism may comprise a hydraulic cylinder and/or a gas cylinder.

The assist mechanism may comprise a brake mechanism. The brake mechanism may comprise, for example, a spring and/or a brake pad. The brake pad may comprise, for example, an expandable gasket. Suitable expandable gaskets include, but are not limited to, pneumatically and hydraulically expandable gaskets.

Another device for delivering and deploying a prosthesis may be provided and comprise an elongate sheath having a sheath lumen and a delivery catheter slidably disposed within the sheath lumen. A means for reducing the retraction force required to retract the sheath over a retraction distance may be provided. In some examples, the reduced retraction force may be greater than or equal to zero over at least a portion of the retraction resistance. Accordingly, an additional force may be required to retract the sheath.

Various methods of deploying a prosthesis are disclosed throughout the specification and in the drawings. In one example, a prosthesis delivery and deployment method comprises the step of providing a device for delivering and deploying a prosthesis. The device may comprise an elongate sheath having a sheath lumen, a prosthesis slidably disposed within the sheath lumen, a delivery catheter slidably disposed within the sheath lumen, and a deployment assist mechanism. The method may further comprise the steps of applying a first retraction force via the deployment assist mechanism to reduce the force required to retract the sheath, and applying a second retraction force to retract the sheath.

DETAILED DESCRIPTION OF PREFERRED EMBODIMENTS

Figure 1:
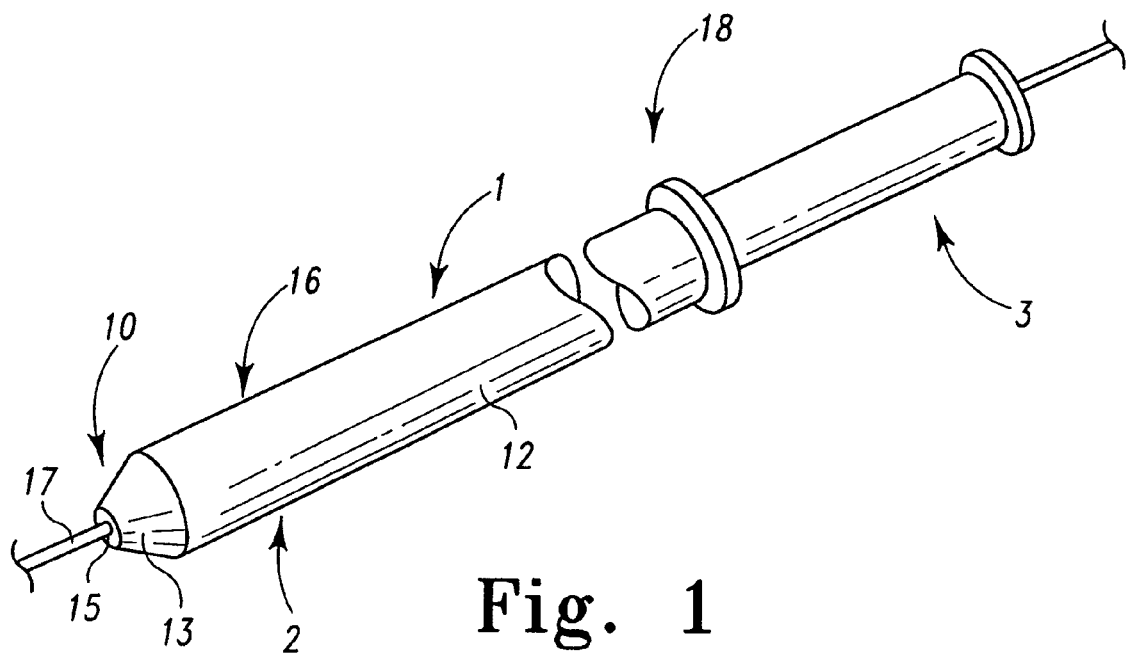
FIG. 1 is a perspective view of an exemplary delivery and deployment device.

Throughout the specification, the terms "distal" and "distally" shall denote a position, direction, or orientation that is generally toward the patient. Accordingly, the terms "proximal" and "proximally" shall denote a position, direction, or orientation that is generally away from the patient.

FIGS. 1-4 show various exemplary devices 1 for delivering and deploying a prosthesis 20 in a body lumen. The device 1 comprises a prosthesis delivery section 2 and an external manipulation section 3. The delivery section 2 travels through the body lumen during the procedure and delivers the prosthesis to a desired deployment site. The external manipulation section 3 stays outside of the body during the procedure. The external manipulation section 3 can be manipulated by the operator to position and release or deploy the prosthesis 20 into the body lumen.

The delivery and deployment device 1 comprises a delivery catheter 10 and a sheath 12. The delivery catheter 10 and the sheath 12 are configured to selectively retain and release a prosthesis 20. The delivery catheter 10 has a proximal end and a distal end. The distal end of the delivery catheter comprises a dilator head 13. The dilator head 13 is distally tapered to provide for atraumatic insertion into the body lumen (not shown). A guidewire lumen 15 extends longitudinally through the delivery catheter 10 between the proximal and distal ends. The delivery catheter 10 is configured to receive a guidewire 17 via the guidewire lumen 15 as shown in FIG. 1.

Figure 2:
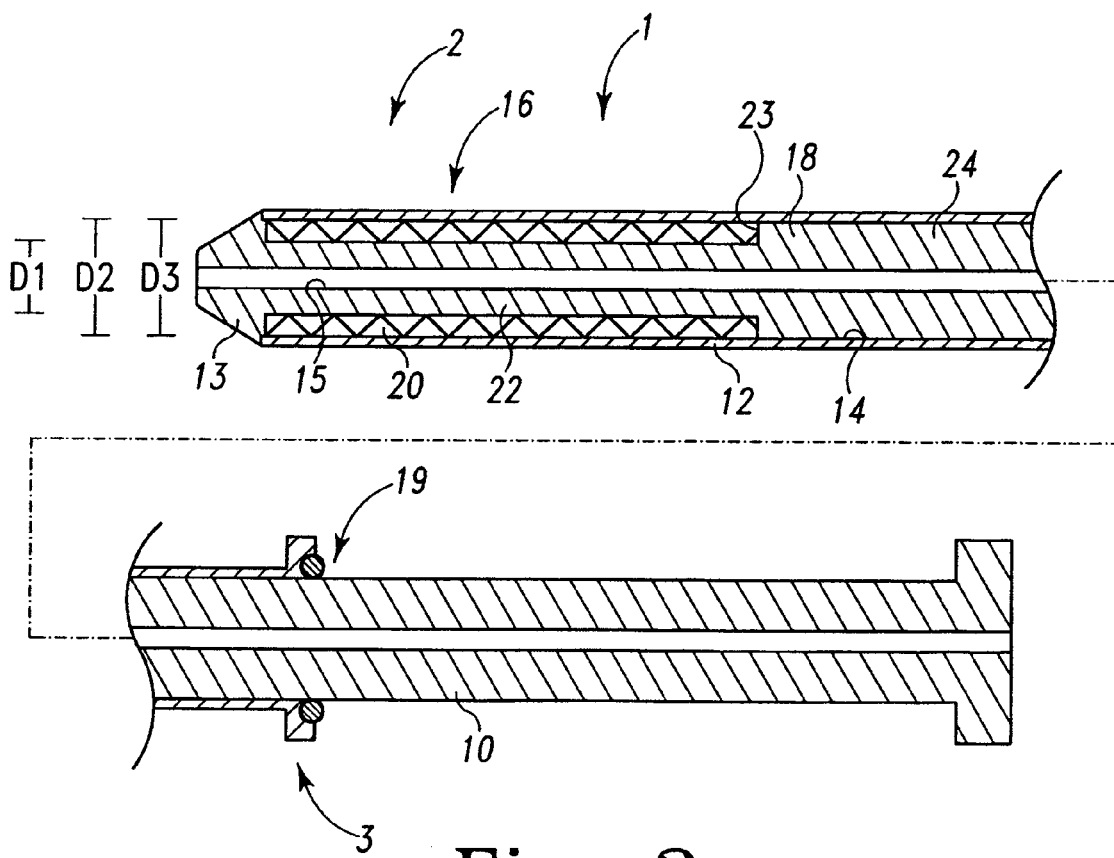
FIG. 2 is a cross-sectional view of the device of FIG. 1.
Figure 3:
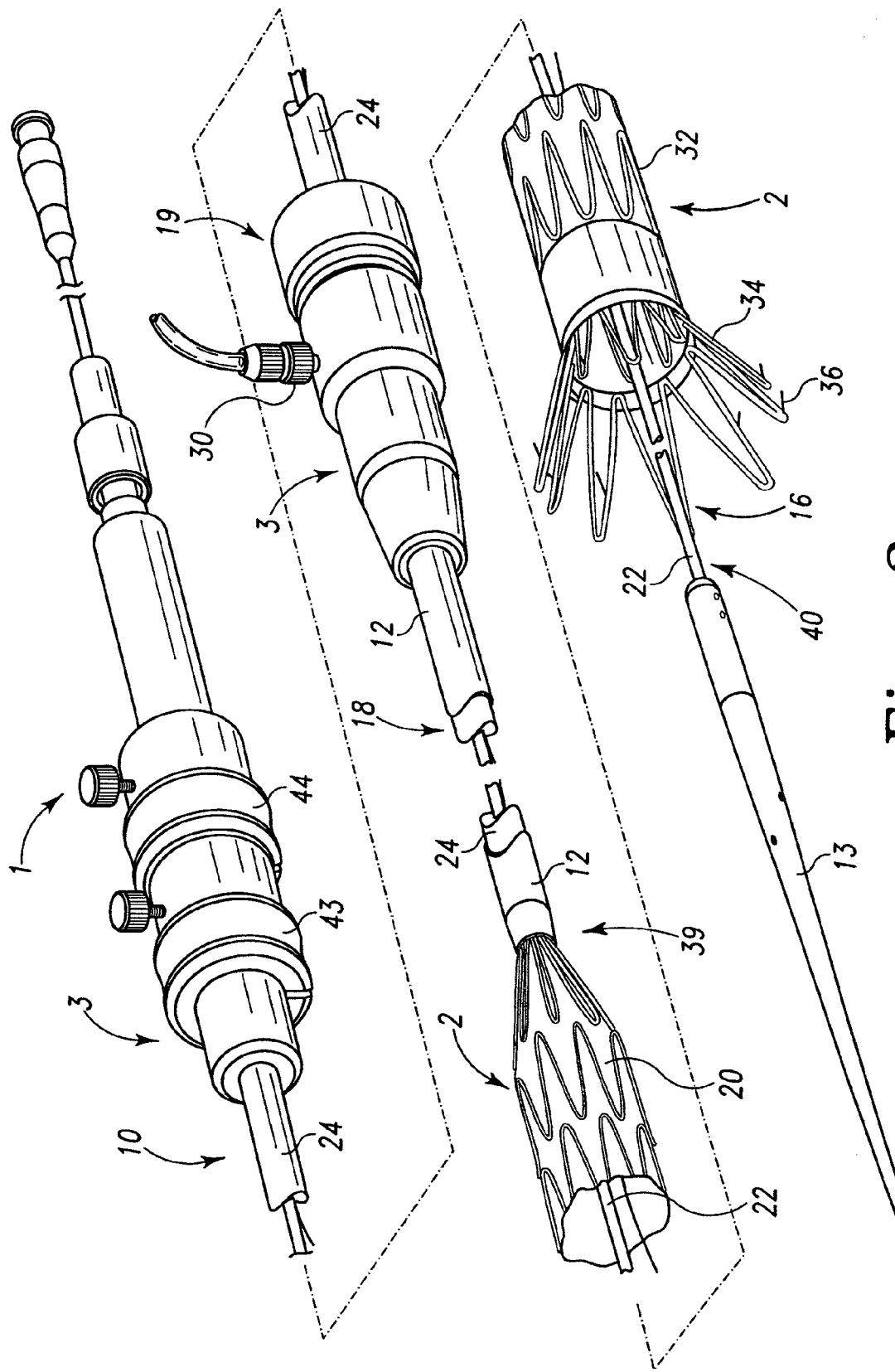
FIG. 3 is a perspective view of selected segments of a delivery and deployment device including a partially-deployed prosthesis.

The delivery catheter 10 comprises a prosthesis receiving portion 16 and a prosthesis release portion 18, as shown in FIG. 2. The receiving portion 16 is disposed on a distal portion of the delivery catheter and is configured to receive the prosthesis 20 in a radially compressed configuration. As shown in FIGS. 2 and 3, the receiving portion 16 may comprise a catheter tube 22 having a longitudinally uniform external diameter D1.

The release portion 18 of the delivery catheter 10 is disposed generally proximally of the prosthesis 20. The release portion 18 can be manipulated, along with the sheath 12, to selectively deliver and deploy the prosthesis 20 in the body lumen. As shown in FIGS. 2 and 3, the release portion 18 may comprise a catheter tube 24 having a longitudinally uniform external diameter D2. Catheter tube 24 may have a diameter D2 that is greater than diameter D1. As shown in FIGS. 2 and 3, the release portion 18 includes a distal-facing annular abutment surface 23 at the transition between catheter tubes 22 and 24. The annular abutment surface 23 faces the proximal end of the prosthesis 20 and is configured to contact the proximal end of the prosthesis 20 during deployment, allowing the delivery catheter 10 to push the prosthesis 20 distally as the sheath 12 is pulled proximally in relation thereto. The delivery catheter 10 may comprise a single unitary structure as shown in FIG. 2. Alternatively, the delivery catheter 10 may comprise a plurality of slidably interconnected catheters 22, 24 as shown in FIG. 3.

The sheath 12 comprises an elongate tubular body having a proximal and distal end and a sheath lumen 14. The sheath lumen 14 has a generally constant diameter between the proximal and distal ends. The sheath 12 extends proximally from the delivery section 2 to the user manipulation section 3. The delivery catheter 10 is slidably disposed within lumen 14. The sheath 12 releasably covers and retains the prosthesis 20 in a radially reduced configuration. The dilator head 13 and the sheath 20 preferably form a generally smooth transition so as to prevent trauma to the body lumen during delivery and deployment. The distal end of the sheath 12 travels within the body lumen during a procedure. The proximal end of the sheath 12 is configured to remain outside of the body during the procedure and can be directly manipulated by the operator to deploy the prosthesis 20.

Figure 4:
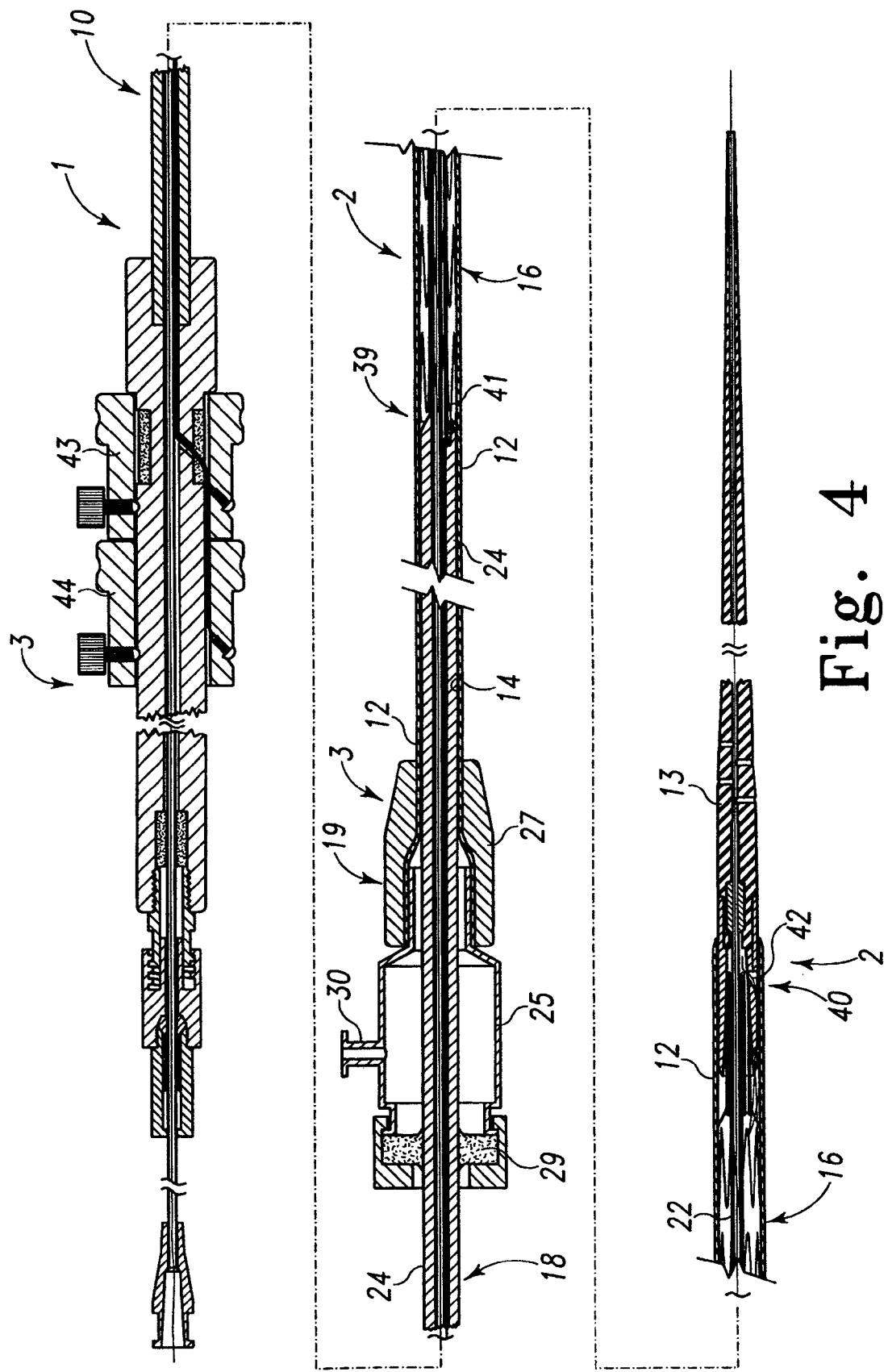
FIG. 4 is a cross-sectional view of the device of FIG. 3.

The sheath 12 may have a length, as shown in FIGS. 3 and 4, that is significantly greater than the length of the prosthesis 20. For example, the sheath 12 may have a length that is two or more times greater than the length of the prosthesis 20. Alternatively, the sheath 12 may have a length that is generally equal to or greater than the length of the prosthesis. The sheath 12 has a uniform internal diameter D3. The internal diameter D3 is generally equal to the external diameter D2 of catheter tube 24 so that the inner surface of the sheath 12 slidingly engages the delivery catheter 10.

The sheath may be made of any suitable biocompatible material, for example PTFE, nylon, or polyethylene. The sheath may optionally comprise a flat wire coil (not shown) to provide the sheath with additional flexibility and kink-resistance. U.S. Pat. No. 5,380,304 and U.S. Published Patent Application Number 2001/0034514 A1, incorporated herein by reference, propose various reinforced sheaths and methods of making the same that may be used in the present invention.

As shown in FIG. 3, the prosthesis 20 may comprise a stent graft having a plurality of self-expanding stents 32. The stents 32 allow the prosthesis 20 to expand during its release from the device 1 and provide support to the prosthesis 20 in its expanded configuration. The stents 32 may cover and/or may be at least partially covered by a graft material. The prosthesis 20 also may include an exposed self-expanding zigzag stent 34 for anchoring the prosthesis 20 in the body lumen. The zigzag stent 34 may comprise barbs 36 that extend from the stent. When the zigzag stent 34 is released, the barbs 36 engage the surrounding lumen.

Various graft materials and configurations may be used in the present invention. Suitable graft configurations include, but are not limited to films, coatings, sheets of biocompatible fabrics, non-woven materials and porous materials. Examples of suitable graft materials include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments.

Stents used in the present invention may be self-expanding or balloon-expandable. A balloon-expandable stent or stent portion may be combined with a self-expanding stent or stent portion. Self-expanding stents can be made of stainless steel, materials with elastic memory properties, such as NITINOL, or any other suitable material. A suitable self-expanding stent includes Z-STENTS®, which are available from Cook, Incorporated, Bloomington, Ind. USA. Balloon-expandable stents may be made of various materials including, but not limited to, stainless steel (typically 316LSS, CoCr, Etc.).

The prosthesis 20 is retained in a radially reduced configuration between the delivery catheter 10 and the sheath 12. The sheath 12 is slidably disposed over the prosthesis 20 and the delivery catheter 10 in a proximal and a distal direction. The sheath 12 may be slid or retracted proximally with respect to the delivery catheter 10 and the prosthesis 20 to expose the prosthesis. To deploy the prosthesis 20, the operator retracts the sheath 12 proximally over the delivery catheter 10 over a retraction distance. Catheter tube 24 pushes the prosthesis 20 distally via the annular abutment surface 23 while the sheath 12 slides proximally in relation thereto. As the sheath 12 slides proximally, the catheter tube 24 pushes the prosthesis 20 distally, expelling the prosthesis 20 from the receiving portion 16 into the body lumen.

As used herein, the term "retraction distance" refers to the total longitudinal distance the sheath must retract over the delivery catheter to remove the prosthesis from the sheath. The retraction distance may be equal to or greater than the length of the prosthesis, for example, when the sheath covers the entire prosthesis. Alternatively, the retraction distance may be less than the length of the prosthesis, for example, when the sheath covers only a portion of the prosthesis.

The delivery and deployment device 1 may further comprise a haemostatic sealing device 19 (shown in FIGS. 3 and 4) for controlling blood loss between the delivery catheter 10 and the sheath 12 during a procedure. An exemplary device 19 includes a haemostatic seal 25 and a clamping collar 27 that clamps the sheath 12 to the haemostatic seal 25. The haemostatic seal 25 may include a seal ring 29 which may be made of silicone. The seal ring 29 engages the delivery catheter 10 and forms a tight haemostatic seal around catheter tube 24. The tight seal between the seal ring 29 and the catheter tube 24 creates an interference fit between the sealing device 19 and the delivery catheter 10, thereby increasing the sliding resistance between the sheath 12 and the catheter 10. The haemostatic sealing device 19 may also include a side tube 30 that facilitates the introduction of medical reagents between the delivery catheter 10 and the sheath 12.

The delivery and deployment device 1 may optionally include deployment control mechanisms 39, 40 as shown in FIGS. 3 and 4. Proximal control mechanism 39 releasably retains the proximal end of the prosthesis 20 and distal control mechanism 40 releasably retains the distal end of the prosthesis 20. Proximal control mechanism 39 may comprise a trigger wire 41 that releasably couples the proximal end of the prosthesis 20 to the delivery catheter 10. Likewise, the distal control mechanism 40 may comprise a trigger wire 42 that releasably couples the distal end of the prosthesis 20 to the delivery catheter 10. The trigger wires 41, 42 extend proximally to the external manipulation section 3 where they are coupled to trigger release devices 43, 44. Trigger release devices 43, 44 are configured to selectively decouple the proximal and distal ends of the prosthesis from the delivery catheter 10, respectively. Various prosthesis retention devices, configurations, and methods of use are disclosed in WO 98/53761, previously incorporated by reference.

The delivery and deployment device 1 has a retraction resistance that results from the interaction between various components of the device, for example the sheath 12, the delivery catheter 10, and the prosthesis 20. The retraction resistance may be expressed in terms of the amount of force that is required to slide the delivery catheter 10 with respect to the sheath 12. In an exemplary system, the retraction resistance may be approximately 100 N, or approximately 22.5 pounds when the prosthesis 20 is fully covered by the sheath 12. Accordingly, the operator will need to apply approximately 22.5 pounds of force to retract the sheath 112. In other examples, the retraction resistance may be less than or greater than 100 N or 22.5 pounds, according to the design and manufacture of the device.

The retraction resistance may be generally constant over the retraction distance, so that a constant retraction force is required to retract the sheath 12 over the entire retraction distance. Alternatively, the retraction resistance may vary over the retraction distance, so that the required retraction force changes over the retraction distance.

In a typical device, the retraction resistance is greatest during the initial stages of deployment, due to static friction and a relatively high area of surface contact between the prosthesis 20 and the sheath 12. Once static friction is overcome, the retraction resistance decreases. Further, as the sheath retracts, the retraction resistance decreases as the area of surface contact between the sheath 12 and the prosthesis 20 decreases.

Figure 5:
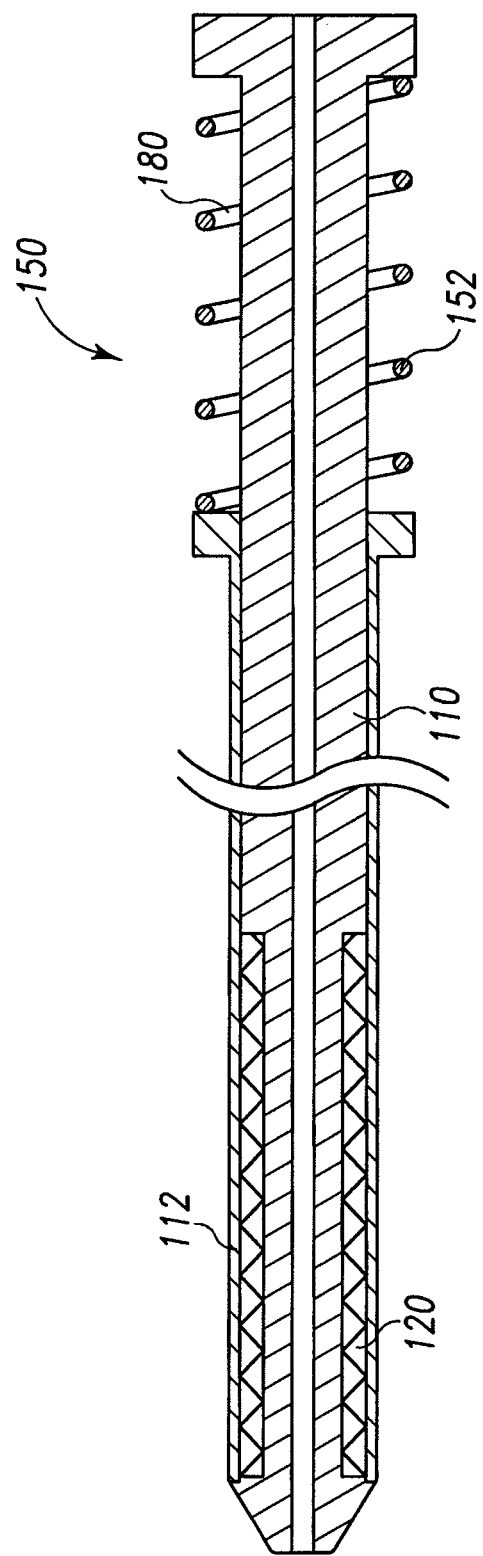
FIGS. 5-8 depict cross-sectional and elevational views of delivery and deployment devices including various exemplary deployment assist mechanisms.

FIG. 5 depicts another device, that is similar to the device shown in FIGS. 1 and 2, for delivering and deploying a prosthesis. The device comprises a delivery catheter 110 and a sheath 112. A prosthesis 120 may be held in a radially compressed configuration between the delivery catheter 110 and the sheath 112. The delivery catheter 110 is configured to expel the prosthesis 120 from the sheath lumen when the sheath 112 retracts over the delivery catheter 110 over a retraction distance. The device may include one or more additional features, as described above.

As shown in FIG. 5, a deployment assist mechanism 150 may be provided. The assist mechanism 150 is configured to provide a retraction force to the delivery and deployment device and may comprise an energy device, for example, a spring 152. As used herein, the term "spring" refers to any resilient or elastic body, device, or combination of bodies or devices that is capable of storing and releasing mechanical energy. Examples of springs include, but are not limited to, coil, helical, leaf, torsion, gas, and v-springs, and other elastic devices such as rubber, plastic, and metallic bands. One or more lock mechanisms, such as release pins, may be provided to fix the sheath 112 to the delivery catheter 110 and to prevent inadvertent sheath retraction.

In the example shown in FIG. 5, the spring 152 includes a coil spring 180. The distal end of the coil spring 180 is coupled to the sheath 112 and the proximal end of the spring 180 is coupled to the delivery catheter 110. When the spring 180 is held in tension, the assist mechanism 150 applies a retraction force to the delivery catheter 110 and the sheath 112. When the retraction force exceeds the retraction resistance, the sheath 112 may retract without additional input. Conversely, when the retraction resistance exceeds the retraction force, the sheath 112 may not retract without additional input.

In one example, the assist mechanism 150 may be configured to apply a retraction force that is greater than the retraction resistance over the entire retraction distance. Accordingly, no manual input is required to retract the sheath 112. One advantage of such an assist mechanism is that no additional manual force is required to deploy the prosthesis 120. On the other hand, the operator may have little or no control over the rate and manner of deployment.

In another example, an assist mechanism 150 may be configured to apply a retraction force that is less than or equal to the retraction resistance over at least a portion of the retraction distance. Accordingly, the sheath 112 will not retract over a corresponding portion of the prosthesis 120 without input from the operator. An advantage of using such an assist mechanism is that it reduces the overall manual force required to retract the sheath 112, but retains the fundamental characteristics and control of a "push-pull" type delivery and deployment device. Consequently, the operator may possess a high degree of control over the rate and manner of deployment, which may minimize the potential for early or inadvertent deployment.

The magnitude of the additional force required to retract the sheath 112 depends on the configuration of the delivery and deployment device and on the configuration of the assist mechanism 150. For example, with a retraction resistance of approximately 22.5 pounds, and an assist mechanism retraction force of approximately 12.5 pounds, the additional force required may be approximately 10 pounds.

As explained above, the retraction resistance of a delivery and deployment device may vary over the retraction distance. An exemplary device may be provided that has a decaying retraction resistance (i.e., the retraction resistance decreases over the retraction distance) and combined with an assist mechanism 150 that is configured to apply a constant force over the entire retraction distance. In one example, the retraction force may be less than the retraction resistance over the entire retraction distance. In another example, the retraction force may be less than the retraction resistance during the initial stages of deployment, and higher than the retraction resistance during the final stages of deployment. In yet another example, the retraction force may be greater than the retraction resistance over the entire retraction distance.

Alternatively, an assist mechanism 150 may be configured to apply a variable force over the entire retraction distance. For example, the assist mechanism 150 may comprise an energy device, such as a spring 152, that is configured to provide a retraction force that decreases as the sheath 112 retracts over the retraction distance. The assist mechanism 150 may have a retraction force that is less than the retraction resistance over the entire retraction distance. In a preferred example, the force decay of the assist mechanism 150 corresponds with the resistance decay of the delivery and deployment device so that the additional force required to retract the sheath is generally constant over the retraction distance. The design and selection of appropriate springs will be readily understood by one of ordinary skill in the art.

Figure 6:
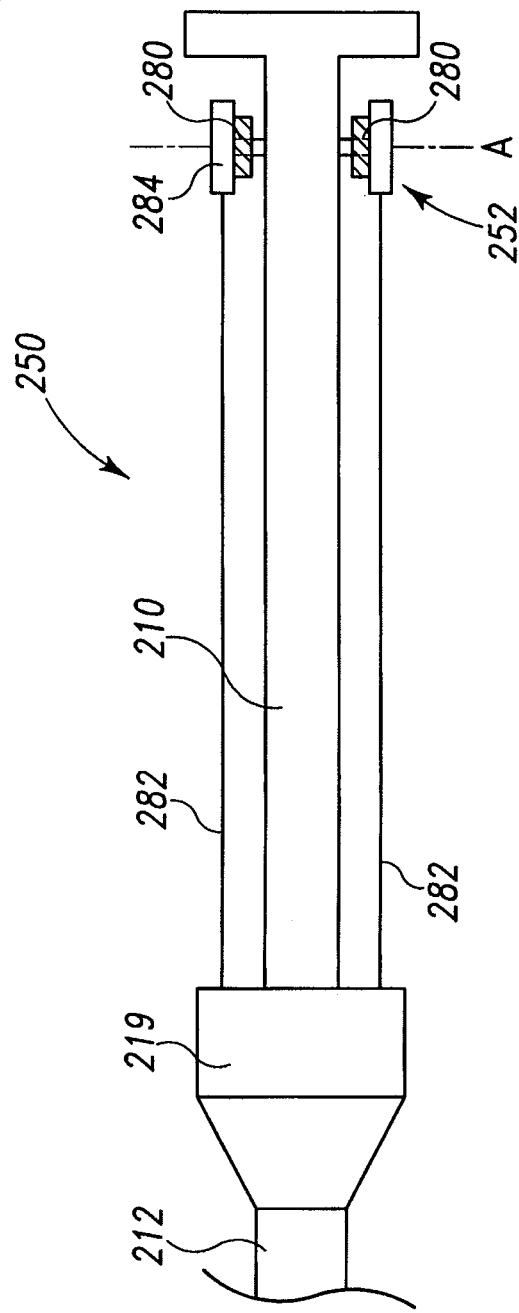

FIG. 6 illustrates a delivery and deployment device and another exemplary deployment assist mechanism 250. The assist mechanism 250 comprises a spring 252 disposed between the delivery catheter 210 and the sheath 212. The spring 252 shown in FIG. 6 comprises two coil springs 280 (e.g., watch springs) and two retractable cables 282. The coil springs 280 are fixed to the delivery catheter 210. The distal ends of the cables 282 are coupled to the sheath 212, for example, via the haemostatic sealing device 219. The proximal ends of the cables 282 are coupled to the delivery catheter 210, via springs 280. During deployment, the coil springs 280 may transmit a retraction force to the sheath 212 via cables 282. The spring 250 may further comprise a spool 284. As the sheath 212 retracts, tension releases in the springs 280, and the cables 282 retract into the spool.

In one example, the retraction resistance of the delivery and deployment device may be approximately 20 pounds and each of the coiled springs 280 may be configured to apply approximately 8 pounds of force continuously to the sheath 212 via cables 282. A locking mechanism (not shown), such as a release pin, may be located along the length of the delivery and deployment device and prevent the sheath from retracting. When the release pin is removed, no sheath movement occurs until the operator provides approximately 4 pounds of additional force. When the operator stops applying force, sheath movement ceases. Deployment may be completed by the combined application of force by the assist mechanism 250 and by the operator. Alternatively, if during retraction, the retraction force of the assist mechanism exceeds the retraction resistance of the delivery and deployment device, deployment may be completed solely by the force of the assist mechanism, without additional operator input.

Figure 7:
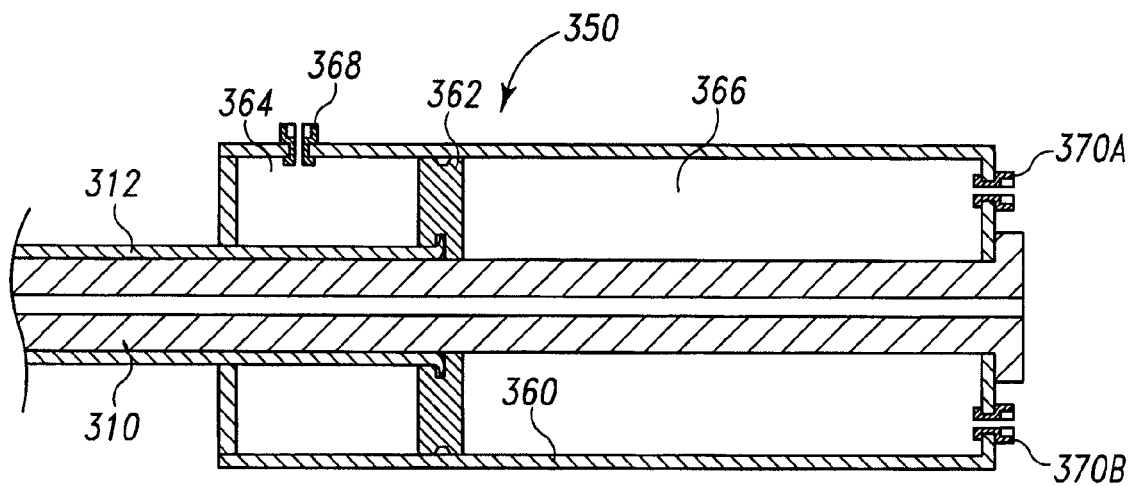

FIG. 7 illustrates a delivery and deployment device and another exemplary deployment assist mechanism 350 comprising an energy device. The mechanism 350 comprises a cylinder 360 and a piston 362 disposed within the cylinder 362. The proximal end of the cylinder 360 is affixed to the delivery catheter 310. The distal end of the cylinder 360 slidingly engages the sheath 312. The piston 362 is affixed to the sheath 312 and is slidingly disposed within the cylinder 360 and about the delivery catheter 310.

The sheath 312, cylinder 360, and piston 362 define a first annular chamber 364. The delivery catheter 310, cylinder 360, and piston 362 define a second annular chamber 366. A seal (not shown) may be provided between the cylinder 360 and the sheath 312, and/or between the cylinder 360 and the delivery catheter 310, to provide a gas and/or fluid-tight seal for the chambers 364, 366. The first and second chambers 364, 366 may each comprise one or more valves. In the example shown in FIG. 7, the first chamber 364 comprises a valve 368 for providing communication to and from the first chamber, and a pair of valves 370A, 370B for providing communication to and from the second chamber. Additionally, or alternatively, a valve may be provided for providing communication between the first and second chambers.

In one example, the assist mechanism 350 comprises a gas spring. For example, the first chamber 364 may be configured to hold a compressible fluid, such as air. The first chamber 364 contains the fluid under pressure so that the fluid exerts a distally-oriented force on the delivery catheter 310 (via the cylinder 360) and a proximally-oriented force on the sheath 312 (via the piston 362). As described above, if the force is greater than the retraction resistance of the delivery and deployment device, the sheath 312 may retract without additional input. Alternatively, if the force is less than the retraction resistance, the sheath 312 may not retract without additional input. Accordingly, the operator may apply an additional force to retract the sheath 312. In either case, as the sheath 312 retracts, the piston 362 slides proximally within the cylinder 360, causing the volume of the first chamber 364 to increase and the pressure within the first chamber 364 to decrease.

As the piston 362 slides within the cylinder 360, the volume of the second chamber 366 decreases. If the second chamber 366 is vented, for example, if the valves 370A, 370B are open, the pressure within the second chamber 366 may remain generally constant. Thus, the resistance within the gas spring may be generally constant over the retraction distance. If, however, the second chamber 366 is sealed, for example if the valves 370A, 370B are closed, the pressure within the second chamber 366 may increase, causing the resistance within the gas spring to increase.

In one example, a delivery and assist mechanism with an initial retraction resistance of approximately 22.5 pounds may be combined with an assist mechanism 350 comprising a gas spring, as described above. The first chamber 364 is charged with pressurized fluid, the second chamber 366 is vented via valves 370A, 370B, and the assist mechanism provides a retraction force of approximately 12.5 pounds.

The operator may apply approximately 10 pounds of force to retract the sheath 312. As the sheath 312 retracts, the piston 362 slides proximally within the cylinder 360 and the pressure within the first chamber 364 decreases. During the initial stages of deployment, the retraction force is generally lower than the retraction resistance. If, during later stages of deployment, the retraction force exceeds the retraction resistance, the sheath 312 will retract without input from the operator. The operator may close one or more of the valves 370A, 370B, to increase the pressure within the second chamber 366, and slow or brake the retraction.

In another example, the first valve 370A may couple the second chamber 366 to a pressure source (not shown) and the second valve 370B may be a vent. When the second valve 370B is closed, the second chamber 366 may be pressurized via the pressure source (not shown). In this configuration, the assist mechanism 350 may act as a brake. The second valve 370B may be opened to depressurize the second chamber 366 and release the brake.

In another example, an assist mechanism 350 may be provided where the first and second chambers 364, 366 each comprise a compression spring. For example, the first chamber 364 may comprise a coil spring (not shown) disposed between the distal end of the cylinder 360 and the piston 362 and the second chamber 366 may comprise a pressurized fluid. The assist mechanism 350 may comprise a valve (not shown) for providing fluid communication between the second chamber 366 and the first chamber 364. Prior to deployment, the first chamber 364 is evacuated, the second chamber 366 is pressurized, the valve between the chambers is closed, and the coil spring (not shown) is compressed. In this configuration, the assist mechanism 350 does not apply a retraction force to the delivery and deployment device. When the valve (not shown) is open, fluid may move from the second chamber 366 to the lower pressure first chamber 364, thus increasing the pressure within the first chamber 364, decreasing the pressure in the second chamber 366, decreasing the resistance on the compression spring, and increasing the retraction force of the assist mechanism 350.

In another example, the assist mechanism 350 may comprise a hydraulic cylinder and include a non-compressible fluid, for example, water or saline solution. In this example, the piston 362 moves within the cylinder 360 by transferring fluid into the first chamber 364. The fluid may be transferred, for example, from a reservoir (not shown) via valve 368. In one example, an inflation-deflation device, such as the Sphere™ Inflation Device by Cook, Incorporated, Bloomington, Ind. USA, could be used to pressurize the first chamber 364. Alternatively, the fluid may be transferred from the second chamber 366 to the first chamber 364 as described above.

In any of the preceding examples, a control system (not shown) may be provided for controlling the pressure within the first and/or second chambers. The control system may comprise, for example, a computer or other suitable input-output device that is capable of predicting or measuring the retraction resistance and actuating one or more valves to effect the retraction force of the assist mechanism. In one example, the control system may comprise a strain gage that measures the retraction resistance during deployment. In another example, stress-strain data (i.e., resistance as a function of retraction distance) for a delivery and deployment device could be empirically or experimentally derived and input into the computer.

Figure 8:
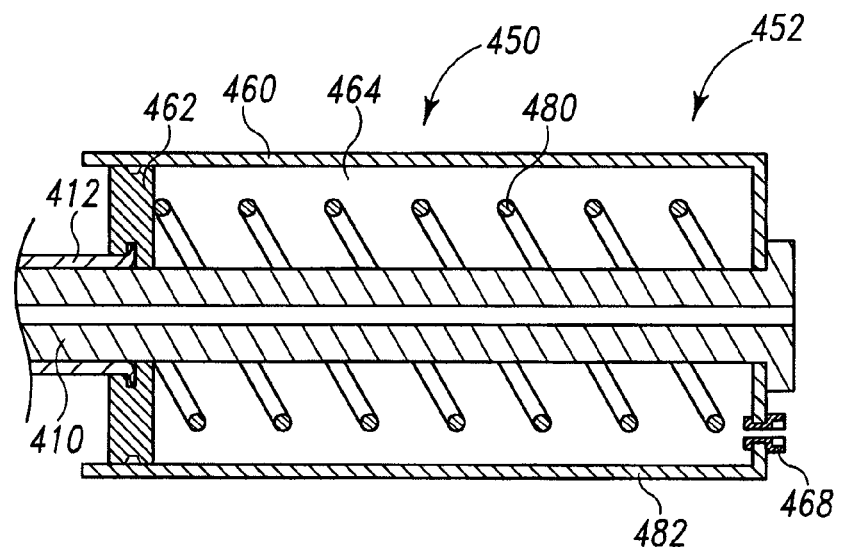

FIG. 8 depicts another deployment assist mechanism 450. Spring 452 is provided and comprises a coil spring 480 and a gas spring 482. The distal end of the coil spring 480 is coupled to the sheath 412 and the proximal end is coupled to the delivery catheter 410. The gas spring 482 comprises a cylinder 460, and a piston 462 disposed within the cylinder 460. The proximal end of the cylinder 460 is affixed to the delivery catheter 410 and the piston 462 is affixed to the sheath 412. The piston 462 is slidably disposed within the cylinder 460 and about the delivery catheter 410. The delivery catheter 410, cylinder 460, and piston 462 define an annular chamber 464. The cylinder 460 may comprise one or more valves 468, as described above.

In one example, the coil spring 480 may be configured to apply approximately 10 pounds of retraction force to a delivery and deployment device having an initial retraction resistance of 15 pounds. Accordingly, the operator will have to apply approximately 5 pounds of additional force to retract the sheath 412.

As explained above, both the retraction resistance of the delivery and deployment device and the retraction force of the coil spring 480 may decay over the retraction distance. If the retraction force decays in proportion with the decay of the retraction resistance, the additional force required of the operator will be generally constant over the retraction distance. If, however, the coil spring force decays too quickly or too slowly, the additional force required by the operator will increase or decrease over the retraction distance.

The gas spring 482 may be provided and operated to selectively resist or assist the restoring force of the coil spring 480, thus selectively decreasing or increasing the retraction force of the assist mechanism 450. For example, the retraction force may be increased by decreasing the pressure in the chamber 464 (e.g., by pulling a vacuum via valve 468). Alternatively, the retraction force may be decreased by increasing the pressure in the chamber 464. Thus, the gas spring may act as a brake. The assist mechanism 450 may comprise a control system (not shown), as described above, for controlling the pressure in the chamber 464.

Figure 9:
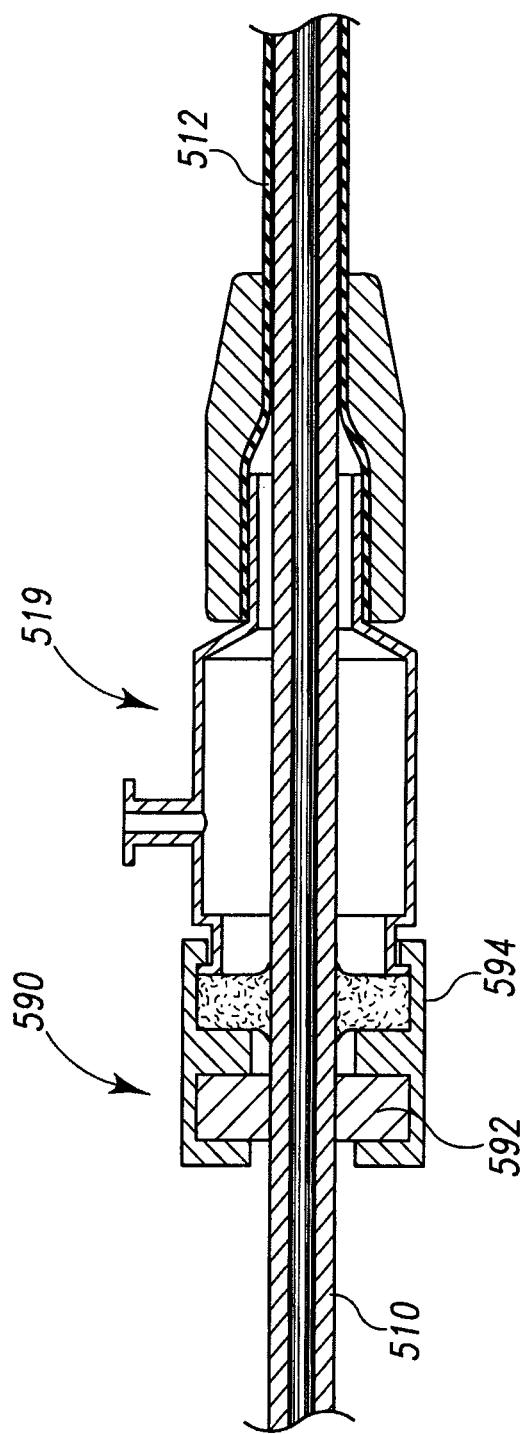
FIG. 9 is a cross-sectional view of a delivery and deployment device including an exemplary brake mechanism.

FIG. 9 depicts another delivery and deployment device that includes a delivery catheter 510, a sheath 512, and a haemostatic sealing device 519 for controlling blood loss between the delivery catheter 510 and the sheath 512. The delivery and deployment device preferably comprises a deployment assist mechanism (not shown), as described above. A brake mechanism 590 may be provided for braking the retraction of the sheath 512 during deployment.

The brake mechanism 590 may comprise a brake pad 592 affixed to the sheath 512 that can be maneuvered to selectively engage and disengage the delivery catheter 510. The brake pad 592 may comprise, for example, a rubber or plastic gasket that is frictionally engageable with the delivery catheter 510. In the example shown in FIG. 9, the brake pad 592 is disposed within a housing 594 that is coupled to sheath 512 via the haemostatic sealing device 519.

The brake mechanism 590 may comprise a flexible handle that is configured to urge the brake pad 592 against the delivery catheter 510 when squeezed or otherwise compressed. In another example, the brake pad 592 may comprise a hydraulically or pneumatically expandable gasket, where the brake pad 592 engages the delivery catheter 510 when the gasket expands.

In all of the preceding examples, a brake mechanism may be used in conjunction with a deployment assist mechanism as a power-release mechanism. As such, the brake mechanism may prevent the release of power from the assist mechanism so that the sheath may be retracted by releasing the brake. Alternatively, a brake mechanism may be used as a power-control mechanism. As such, the brake mechanism may allow the release of power from the assist mechanism and the sheath may be controlled via selective application of the brake. The brake mechanism may be actuated manually by the operator, or automatically, for example, by a control system (not shown), as described above.

Figure 10A:
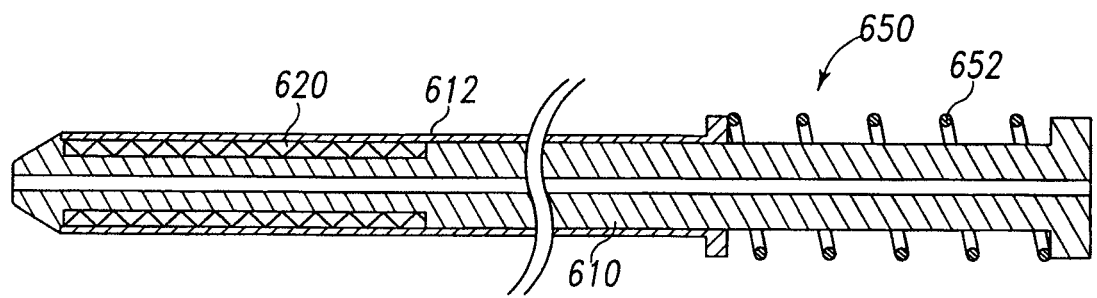
FIGS. 10A-10C are cross-sectional views of a delivery and deployment device in various stages of deployment.
Figure 10B:
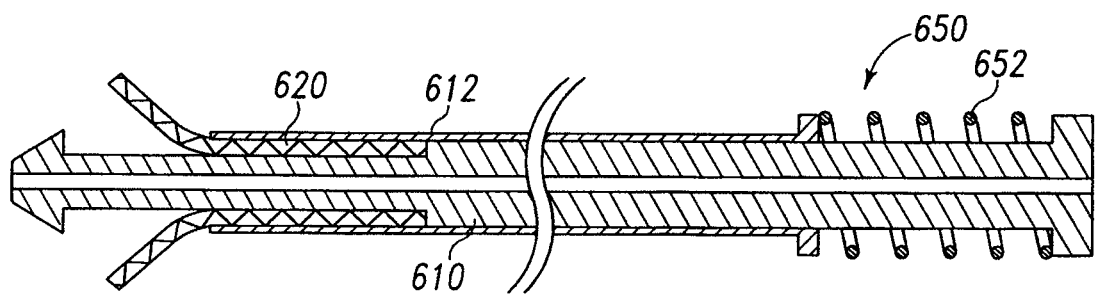
Figure 10C:
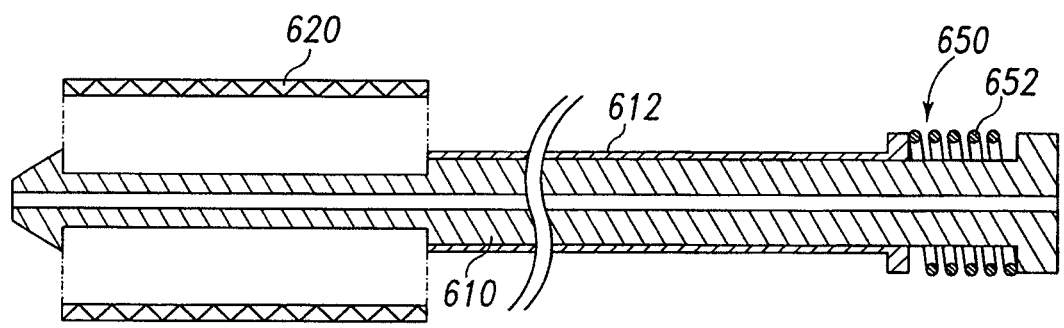

FIGS. 10A-10C illustrate a method of deploying a prosthesis in a body lumen. First, a guidewire (not shown) is introduced into the body lumen and advanced until the tip is beyond the region where the prosthesis 620 will be deployed. The delivery and deployment device is then inserted into the body lumen over the guide wire (not shown) and positioned in the treatment area by radiographic techniques that are generally known in the art. At this stage, the prosthesis 620 is fully retained in the delivery and deployment device in a radially-constrained configuration by the sheath 612 as shown in FIG. 10A.

Once the prosthesis 620 is properly positioned, the device is ready for deployment. If the delivery and assist mechanism comprises a lock mechanism, it may be removed. To deploy the prosthesis 620, the operator may use a deployment assist mechanism 650. In the example shown in FIGS. 10A-10C, the assist mechanism 650 comprises a spring 652, although any suitable energy device may be used. The assist mechanism 650 applies a retraction force to the delivery and deployment device. In a preferred example, the retraction resistance is initially greater than the retraction force applied by the assist mechanism 650. Accordingly, the sheath will not retract until the operator applies an additional retraction force.

The operator may retract the sheath 612, for example, by pulling the sheath 612 in a proximal direction and pushing the delivery catheter 610 in a distal direction. As the sheath 612 retracts, the prosthesis 620 becomes exposed and is allowed to expand into the body lumen. If the prosthesis 620 is self-expanding, it may expand simply by removing the sheath, as shown in FIG. 10B.

In order to maintain proper prosthesis positioning in the body lumen, the delivery catheter 610 is held steady relative to the sheath 612 during deployment. The operator may manually fix the position of the delivery catheter 610. Alternatively, a delivery fixture (not shown) may be provided to hold the delivery catheter 610 steady during deployment.

When the retraction force of the assist mechanism 650 is less than or equal to the retraction resistance, the operator may have increased control over the deployment. For example, the operator can halt sheath retraction, simply by removing pressure from the sheath. When the retraction force of the assist mechanism 650 is greater than or equal to the retraction resistance, the operator may have reduced control over the deployment. Accordingly, a brake mechanism may be provided, as described above.

FIG. 10C shows the delivery and deployment device in a fully deployed state, where the sheath 612 is fully retracted over the retraction distance and the prosthesis 620 is expanded within the body lumen. The delivery and deployment device and the guide wire may now be removed from the body lumen.

Throughout this specification various indications have been given as to preferred and alternative embodiments of the invention. However, it should be understood that the invention is not limited to any one of these. It is therefore intended that the foregoing detailed description be regarded as illustrative rather than limiting, and that it be understood that it is the appended claims, including all equivalents, that are intended to define the spirit and scope of this invention.

What is claimed is:

1. A device for delivering and deploying a prosthesis comprising:
   an elongate sheath having a sheath lumen;
   a delivery catheter slidably disposed within the sheath lumen; and
   a deployment assist mechanism comprising a stored energy device having a proximal end coupled to the delivery catheter and a distal end coupled to the sheath and configured to apply a retraction force, independent of a manual force required to retract the sheath, to both the delivery catheter and the sheath;
   where the sheath is retractable over the delivery catheter over a retraction distance; and
   where the device has a retraction resistance and the stored energy device applies the retraction force that is at the same time greater than zero and less than or equal to the retraction resistance over a length of the retraction distance, during manual retraction of the sheath,
   wherein the direction of the retraction force applied by the stored energy device is substantially parallel with the sheath.

2. The device of claim 1, where the retraction force is greater than or equal to the retraction resistance over at least another length of the retraction distance.

3. The device of claim 1, where the retraction resistance decreases as the sheath is retracted over the delivery catheter.

4. The device of claim 3, where the retraction force decreases as the sheath is retracted over the delivery catheter.

5. The device of claim 1, where the retraction force decreases as the sheath is retracted over the delivery catheter.

6. The device of claim 1, where the stored energy device comprises a spring.

7. The device of claim 6, where the spring comprises one or more coil springs.

8. The device of claim 7, where the spring comprises one or more gas springs.

9. The device of claim 6, where the spring comprises one or more gas springs.

10. The device of claim 1, where the assist mechanism comprises a hydraulic cylinder.

11. The device of claim 1, where the stored energy device comprises a pneumatic cylinder.

12. The device of claim 11, where the stored energy device further comprises a compression spring.

13. The device of claim 1, further comprising a brake mechanism.

14. The system of claim 13, where the brake mechanism comprises a spring.

15. The device of claim 13, where the brake mechanism comprises an expandable gasket.

16. The system of claim 15, where the gasket is pneumatically expandable.

17. The system of claim 15, where the gasket is hydraulically expandable.

18. The device of claim 1, further comprising any two or more of the following:
   the retraction force is greater than or equal to the retraction resistance over at least another distance of the retraction distance;
   the retraction resistance decreases as the sheath is retracted over the delivery catheter;
   the retraction force decreases as the sheath is retracted over the delivery catheter; and
   the stored energy device comprises a spring comprising one or more coil springs;
   the stored energy device comprises a spring comprising one or more gas springs;
   the stored energy device comprises a hydraulic cylinder;
   the stored energy device comprises a pneumatic cylinder;
   a brake mechanism;
   a brake mechanism comprising a spring;
   a brake mechanism comprising a pneumatically expandable gasket; and
   a brake mechanism comprising a hydraulically expandable gasket.

19. A device for delivering and deploying a prosthesis comprising:
   an elongate sheath having a sheath lumen;
   a delivery catheter slidably disposed within the sheath lumen; and a means for reducing the retraction force required to manually retract the sheath over the delivery catheter over a retraction distance;
where the reduced retraction force in a longitudinal direction is greater than zero over a length of the retraction distance, during manual retraction of the sheath,
wherein the means for reducing the retraction force comprises a stored energy device having a distal end coupled to the sheath and a proximal end coupled to the delivery catheter that applies a force to both the sheath and the delivery catheter in a direction substantially parallel with the sheath.

\* \* \* \* \*